United States Patent
Taylor

(10) Patent No.: US 9,193,715 B2
(45) Date of Patent: Nov. 24, 2015

(54) REGULATION OF CHOLESTEROL HOMEOSTASIS

(71) Applicant: Richard Taylor, South Bend, IN (US)

(72) Inventor: Richard Taylor, South Bend, IN (US)

(73) Assignee: University of Notre Dam du Lac, Notre Dame, IN (US)

( * ) Notice: Subject to any disclaimer, the term of this patent is extended or adjusted under 35 U.S.C. 154(b) by 0 days.

(21) Appl. No.: 14/519,059

(22) Filed: Oct. 20, 2014

(65) Prior Publication Data

US 2015/0038566 A1 Feb. 5, 2015

Related U.S. Application Data

(62) Division of application No. 13/961,659, filed on Aug. 7, 2013, now Pat. No. 8,865,761.

(60) Provisional application No. 61/742,290, filed on Aug. 7, 2012.

(51) Int. Cl.
| | |
|---|---|
| *C07D 407/06* | (2006.01) |
| *C07D 309/06* | (2006.01) |
| *C07D 303/28* | (2006.01) |
| *C07D 303/14* | (2006.01) |
| *A61K 31/351* | (2006.01) |

(52) U.S. Cl.
CPC ............ *C07D 407/06* (2013.01); *A61K 31/351* (2013.01); *C07D 303/14* (2013.01); *C07D 303/28* (2013.01); *C07D 309/06* (2013.01)

(58) Field of Classification Search
USPC .......................................... 514/451; 549/414
See application file for complete search history.

(56) References Cited

U.S. PATENT DOCUMENTS

| | | | |
|---|---|---|---|
| 5,719,179 | A | 2/1998 | Mizukami et al. |
| 6,365,577 | B1 | 4/2002 | Iversen |
| 7,300,921 | B2 | 11/2007 | McAlpine et al. |
| 7,375,088 | B2 | 5/2008 | Bachmann et al. |
| 8,008,049 | B2 | 8/2011 | Machida et al. |
| 2003/0191110 | A1 | 10/2003 | Botfield et al. |
| 2009/0227602 | A1 | 9/2009 | Griffin et al. |
| 2010/0055037 | A1 | 3/2010 | Wands et al. |
| 2011/0295023 | A1 | 12/2011 | Machida et al. |

FOREIGN PATENT DOCUMENTS

JP 2004269465 A 9/2004

OTHER PUBLICATIONS

Blakemore et al., "A synthesis of herboxidiene," J. Chem. Soc., Perkin Trans. 1 (1999) pp. 955-968.
Chang et al., "Neuronal Cholesterol Esterification by ACAT1 in Alzheimer's Disease," IUBMB Life (Apr. 2010) 62 (4): 261-267.
Edmunds et al., "Synthesis of Simplified Herboxidiene Aromatic Hybrids," Bioorganic & Medicinal Chemistry Letters 10 (2000) pp. 1365-1368.
Ghosh et al., "A Stereoselective Synthesis of (+)-Herboxidiene/GEX1A," Organic Letters (2011) 13 (1): 66-69.
Greer et al., "The Nova Scotia (Type D) Form of Niemann-Pick Disease Is Caused by a G3097 T Transversion in NPC1," Am. J. Hum. Genet. (1998) 63: 52-54.
Hasegawa et al., "Identification of SAP155 as the Target of GEX1A (Herboxidiene), an Antitumor Natural Product," ACS Chem. Biol. (2011) 6: 229-233.
Kotake et al., "Splicing factor SF3b as a target of the antitumor natural product pladienolide," Nature Chemical Biology (Sep. 2007) 3 (9): 570-575.
Patterson, "Niemann-Pick Disease Type C," GeneReviews—NCBI Bookshelf 22 [http://www.ncbi.nlm.nih.gov/books/NBK1296] (Jan. 26, 2000).
Pipalia et al., "Histone deacetylase inhibitor treatment dramatically reduces cholesterol accumulation in Niemann-Pick type C1 mutant human fibroblasts," PNAS (Apr. 5, 2011) 108 (14): 5620-5625.
Shao et al., "Identification of the Herboxidiene Biosynthetic Gene Cluster in Streptomyces chromofuscus ATCC 49982," Applied and Environmental Microbiology (Jan. 13, 2012) pp. 2034-2038.
Zhang et al., "Total Synthesis of Herboxidiene/GEX 1A," American Chemical Society; Organic Letters (2007) 9 (16): 3141-3143.

*Primary Examiner* — Kristin Vajda
(74) *Attorney, Agent, or Firm* — Haukaas Fortius PLLC; Michael H. Haukaas

(57) ABSTRACT

The invention provides novel compounds of Formulas (I)-(IV), as described herein. Also provided are compositions of these compounds, method of making the compounds, and methods of using the compounds. The compounds can be used to regulate cholesterol homeostasis and to treat conditions and diseases associated with cholesterol homeostasis, including lysosomal lipid storage disorders such as Niemann-Pick Disease type C.

17 Claims, 3 Drawing Sheets

REGULATION OF CHOLESTEROL HOMEOSTASIS

RELATED APPLICATIONS

This application is a continuation of U.S. patent application Ser. No. 13/961,659, filed Aug. 7, 2013, issued as U.S. Pat. No. 8,865,761, and this application claims priority under 35 U.S.C. §119(e) to U.S. Provisional Patent Application No. 61/742,290, filed Aug. 7, 2012, the specifications of which are herein incorporated by reference.

BACKGROUND OF THE INVENTION

Niemann-Pick Disease type C (NPC) is a neurovisceral lysosomal lipid storage disorder that has a wide clinical spectrum. The disease may cause rapid fatality in neonates, or chronic neurodegenerative symptoms in children and adults. It can present hepatosplenomegaly (enlarged liver and spleen) in infants, children or adults. NPC is characterized by eye movement abnormalities, dysphagia (difficulty in swallowing) and dysarthria (slurred, irregular speech), ataxia (lack of muscle control), and progressive cognitive dysfunction (progressive intellectual decline) leading to dementia. NPC is also associated with impaired intracellular lipid trafficking, including the pathways for cholesterol, leading to lipid accumulation in the liver, spleen, and in the brain.

Based on molecular genetic testing, the cause of NPC has been identified as associated with autosomal recessively inherited loss-of-function mutations in in either the NPC1 or NPC2 genes. Niemann-Pick disease type D (NPD), previously and still sometimes used to describe the genetic isolate from Nova Scotia, is now associated with mutations in the NPC1 gene. The two genes regulate cholesterol homeostasis. NPC1 encodes a putative integral membrane protein containing sequence motifs consistent with a role in intracellular transport of cholesterol to post-lysosomal destinations. This protein binds cholesterol at its N-terminal domain and transports cholesterol to late endosomal/lysosomal compartments where they are hydrolyzed and released as free cholesterol. Defects in this gene, which account for 95% of NPC cases, cause over-accumulation of cholesterol and glycosphingolipids in late endosomal/lysosomal compartments. The NPC2 gene encodes a protein containing a lipid recognition domain that binds and transports cholesterol to the NPC1 protein. Mutation in NPC2 accounts for approximately 4% of NPC cases.

The diagnosis of NPC is confirmed by biochemical testing that demonstrates impaired cholesterol esterification and positive filipin staining in cultured fibroblasts. Biochemical testing to detect carrier status is unreliable. Most individuals with NPC have NPC1, caused by mutations in NPC1; fewer than 20 individuals have been diagnosed with NPC2, caused by mutations in NPC2. Molecular genetic testing of NPC1 and NPC2 detects disease-causing mutations in approximately 94% of individuals with NPC.

Treatment options for NPC are limited. Traditional treatment plans use medicines that aim to control or relieve specific symptoms of the disease. Currently, there is no FDA approved medicine that specifically targets NPC. Only one drug, miglustat (N-butyl-deoxynojirimycin), has been approved in Europe and other countries for the treatment of NPC. Therefore, a need still exists for novel and more effective methods of treating NPC.

GEX1A and pladienolide have previously been found to have respective antitumor activities (U.S. Pat. No. 5,719,179 (Mizukami et al.) and U.S. Pat. No. 8,008,049 (Machida et al.)). GEX1A was isolated in 1992 by researchers at the Monsanto Agricultural Company from microbial fermentation broths of *Streptomyces chromofuscus*, due to its herbicidal activity. GEX1A was later found to upregulate low density lipoprotein (LDL) receptor and lower plasma cholesterol. However, the plasma cholesterol cycle is separated by the blood-brain barrier from the central nervous system, where the accumulation of unesterified cholesterol is observed in the NPC phenotype. Accordingly, new therapies for the treatment of lysosomal lipid storage disorders such as NPC are needed. For example, new therapies that reduce cellular cholesterol storage are needed to improve current clinical therapies.

SUMMARY

The invention provides compounds and compositions that afford pharmacological benefits in regulating cholesterol homeostasis in mammals. The invention also provides methods of the preparation of such compounds and compositions, and methods of their use. The compounds and compositions can be useful, for example, for the treatment and management of a variety of diseases including neurodegenerative diseases and lysosomal storage disorders, including disorders characterized by an accumulation of cholesterol. The therapeutic compositions can include other therapeutic agents compatible with the compounds described herein.

The invention thus provides compound of Formula I:

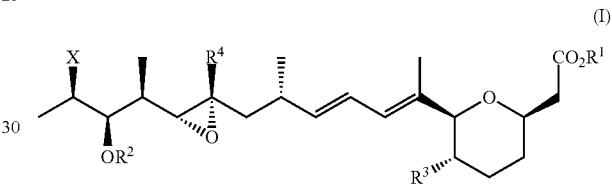

wherein
X is OH, alkoxy (e.g., $OCH_3$), or H;
$R^1$ is H, alkyl (e.g., $CH_3$), cycloalkyl, amino, aryl, or heterocycle; $R^2$, $R^3$, and $R^4$ are each independently H or alkyl (e.g., $CH_3$), provided that either $R^3$ or $R^4$ is H; or a pharmaceutically acceptable salts thereof. The alkyl, alkoxy, cycloalkyl, amino, aryl, and heterocycle groups can be optionally substituted with one or more substituents, as defined below in the definition of substituent.

The invention also provides for a method of synthesizing a compound of Formula I via cross metathesis by reacting a compound of Formula II:

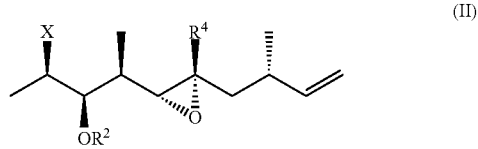

wherein X, $R^2$, and $R^4$ are as defined for Formula I; and a compound of Formula III:

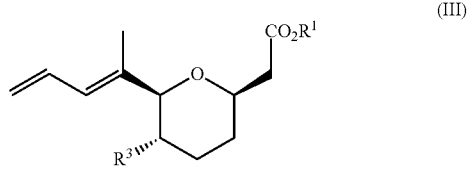

wherein $R^1$ and $R^3$ are as defined for Formula I, to provide the compound of Formula I. The synthesis can be carried out under cross metathesis coupling conditions. The compound of Formula I can be isolated and/or purified. The catalyst may be the Grubbs-Hoveyda catalyst. The invention therefore also provides novel compounds of Formulas (II) and (III).

The invention also provides compounds of Formula (IV) and methods of treating or managing neurodegenerative diseases and lysosomal storage disorders in a subject by administering to the subject an effective amount of a compound of Formula (IV):

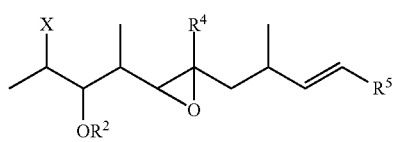

(IV)

wherein
X is H, OH, or alkoxy (e.g., OCH₃);
R² is H or alkyl (e.g., CH₃);
R⁴ is H or alkyl (e.g., CH₃); and
R⁵ is alkyl (e.g., CH₃), cycloalkyl, aryl, heterocycloalkyl, or alkyl(heterocycloalkyl), each optionally substituted. Accordingly, in one embodiment, R⁵ can be a moiety of Formula (V):

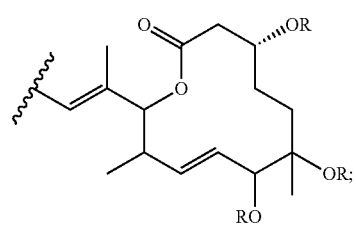

(V)

wherein each R is independently H, R¹ as defined for Formula I, or an oxygen protecting group (e.g., —Ac, —Bz, or —Bn); or a moiety of Formula (VI):

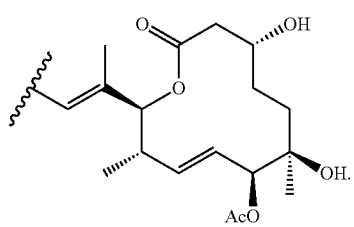

(VI)

The methods can include modulating cholesterol transport, and/or reducing cellular cholesterol storage in a cell, for example, compared to the cholesterol storage in the absence of the treatment. The reduction (e.g., inhibition) of cholesterol storage can be, for example, more than 10%, more than 20%, more than 30%, more than 40%, more than 50%, more than 60%, or more than 75%, compared to the storage found in the cell in the absence of contacting the cell with the compound of Formula (IV).

The invention further provides methods of preparing a compound of Formula (IV) comprising oxidizing GEX1A (herboxidiene) or a *Streptomyces chromofuscus* extract to form a compound of Formula II and a compound of Formula III, synthetically modifying the compounds, and linking the resulting derivatives together using olefin cross metathesis.

In one embodiment, the neurodegenerative diseases or lysosomal storage disorders being treated demonstrate a neurovisceral accumulation of cholesterol. In some embodiments, the accumulation of cholesterol is the phenotype of NPC or NPD. In another embodiment, the disease is Alzheimer's disease. The subject of treatment can be a mammal, such as a human.

In one embodiment, the compound of Formula (IV) is a compound of Formula (I). In another embodiment, the compound of Formula (IV) is the compound GEX1A:

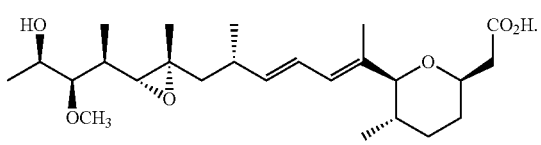

GEX1A (herboxidiene)

In yet another embodiment, the compound of Formula (IV) is pladienolide B:

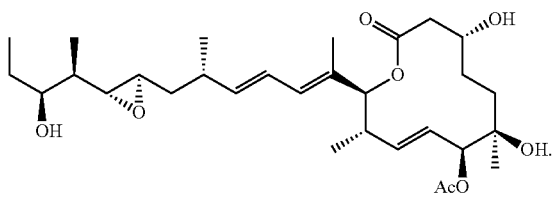

pladienolide B

The invention thus provides novel compounds of the formulas described herein, intermediates for their synthesis, as well as methods of preparing the compounds and formulas. The invention also provides compounds of the formulas described herein that are useful as intermediates for the synthesis of other useful compounds. The invention further provides for the use of the compounds and their corresponding compositions for the treatment of neurodegenerative diseases or lysosomal storage disorders in a mammal, such as a human. The compositions can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1A:
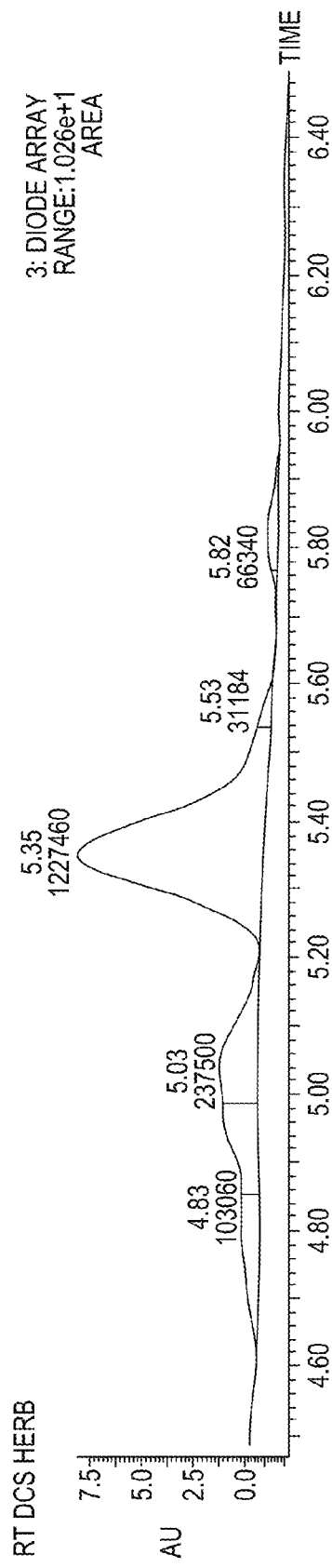
FIG. 1. Liquid chromatography-mass spectrometry (LC-MS) analysis of the fermentation and extraction of GEX1A from *S. chromofuscus*. (A) UV trace of an *S. chromofuscus* extract with integration; (B) UV trace of the *S. chromofuscus* extract; (C) ion extraction for GEX1A (ES-M-1/z-437.38); (D) total ion current (TIC) of the *S. chromofuscus* extract.
Figure 1B:
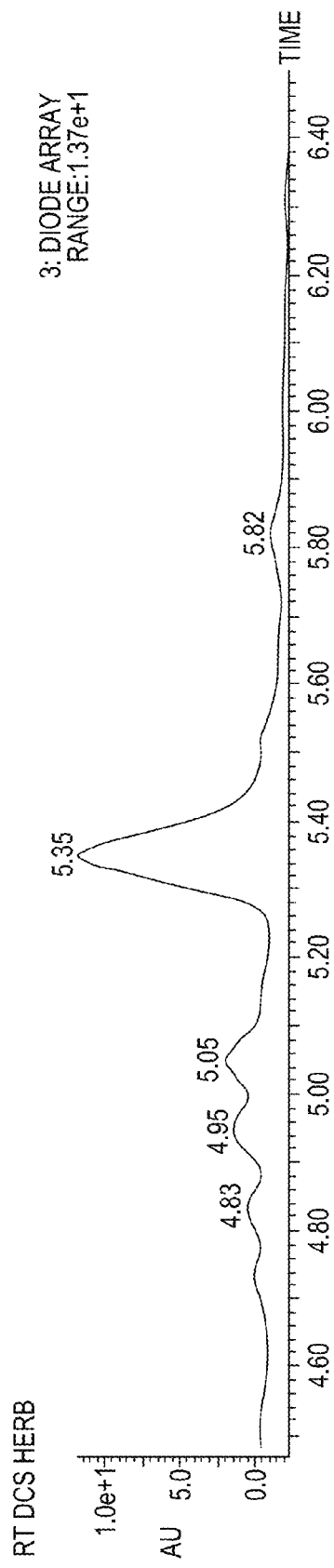
Figure 1C:
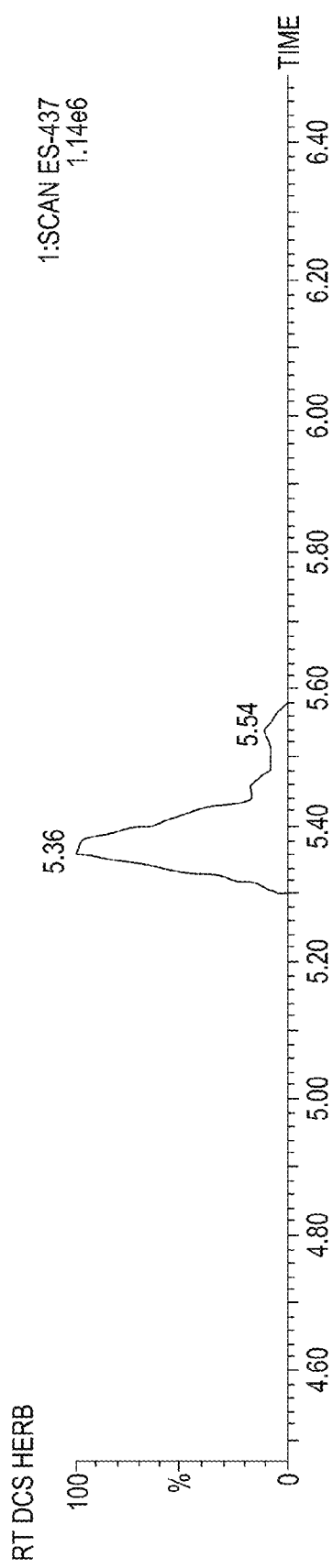
Figure 1D:
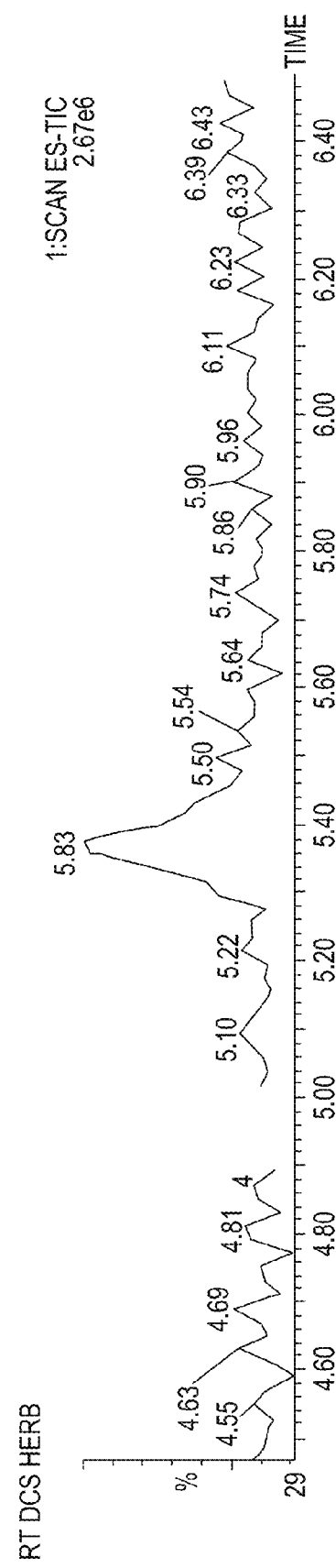

Recent studies that histone deacetylase (HDAC) inhibitors can correct cholesterol storage defects in human NPC1 mutant cells provide the potential basis for treatment options for NPC disease. Presumably, the HADC inhibitor, panobinostat, can correct cholesterol homeostasis through its ability to broadly upregulate gene expression. Herboxidiene is a *Streptomyces*-derived polyketide with anti-tumor activity. Herboxidiene's ability to upregulate gene expression is similar to trichostatin A, a known HDAC inhibitor. However, herboxidiene does not affect histone acetylation but has recently been shown interact with SP155 and inhibit pre-RNA splicing. Based on these findings, we sought to investigate herboxidiene's potential to affect cholesterol levels in NPC cells. Preliminary studies indicate that herboxidiene is equipotent to HDAC inhibitors in the classic filipin assay on NPC cells.

Herboxidiene, a natural product isolated from *Streptomyces chromofuscus*, is currently being fermented in a laboratory setting. Herboxidiene has been previously shown to have anticancer activity through a unique mechanism. Significant quantities of herboxidiene have been isolated and the compound is being used for preparing novel derivative compounds. Based on its mode of action, herboxidiene may reverse the effects of cholesterol storage in NPC cells. The structure-activity relationships related to herboxidiene for the treatment of NPC disease are being evaluated. Through these efforts, new chemical entities based on herboxidiene have been identified for the treatment of Niemann-Pick Type C disease, other lysosomal storage disorders, as well as other related indications.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

For a synthetic reaction, an "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

For a therapeutic treatment or biological reaction, an "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. Thus, a therapeutically effective amount of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

A "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The compounds described herein can inhibit an enzyme or a biochemical pathway. The terms "inhibit", "inhibiting", and "inhibition" refer to the slowing, halting, or reversing the growth or progression of a disease, infection, condition, pathway, or group of cells. The inhibition can be greater than about 20%, 40%, 60%, 80%, 90%, 95%, or 99%, for example, compared to the growth or progression that occurs in the absence of the treatment or contacting.

The term "alkyl" refers to a saturated straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. The term "alkyl" can include "alkenyl" and "alkynyl" moieties. An alkyl can be substituted with a cycloalkyl. An example of a cycloalkyl group substituted with an alkyl is 1-ethyl-4-methyl-cyclohexyl, and the group can be attached to a compound at any carbon atom of the group.

The term "cycloalkyl" refers to a cyclic hydrocarbon having from 1 to 20 (e.g., 1 to 10 or 1 to 6) carbon atoms. Examples of cycloalkyl groups include, but are not limited to, cyclopropyl, cyclobutyl, cyclopentyl, cyclohexyl, and adamantyl.

The term "alkenyl" refers to a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

The term "alkoxy" refers to an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

The term "aryl" refers to an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

The term "heteroalkyl" refers to an alkyl moiety in which at least one of its carbon atoms has been replaced with a heteroatom (e.g., N, O or S).

The term "heteroaryl" refers to an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

The term "heteroarylalkyl" refers to a heteroaryl moiety bound to an alkyl moiety.

The term "heterocycle" refers to an aromatic, partially aromatic or non-aromatic, monocyclic or polycyclic ring or ring system comprised of carbon, hydrogen and at least one heteroatom (e.g., N, O or S). A heterocycle may comprise multiple (i.e., two or more) rings fused or bound together. Heterocycles can include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

The term "heterocycloalkyl" refers to a non-aromatic heterocycle.

The term "substituted," when used to describe a chemical structure or moiety, refers to a derivative of that structure or moiety wherein one or more of its hydrogen atoms is substituted with a chemical moiety or functional group such as, but not limited to, alcohol (e.g., hydroxyl, alkyl-OH), aldehyde, alkanoyloxy, alkoxycarbonyl, alkyl (e.g., methyl, ethyl, propyl, t-butyl), alkenyl, alkynyl, alkylcarbonyloxy (—OC(O)R), amide (—C(O)NHR— or —RNHC(O)—), amidinyl (—C(NH)NHR or —C(NR)NH$_2$), amine (primary, secondary and tertiary such as alkylamino, arylamino, arylalkylamino), aroyl, aryl, aryloxy, azo, carbamoyl (—NHC(O)OR— or —OC(O)NHR—), carbamyl (e.g., —CONH$_2$, as well as CONH-alkyl, CONH-aryl, and CONH-arylalkyl (e.g., Bn)), carbonyl, carboxyl, carboxylic acid, carboxylic acid anhydride, carboxylic acid chloride, cyano, ester, epoxide, ether (e.g., methoxy, ethoxy), guanidino, imine (primary and secondary), isocyanate, isothiocyanate, ketone, halo (F, Cl, Br, or I), haloalkyl (e.g., fluoromethyl, difluoromethyl, trifluoromethyl), hemiacetal, heterocycle, nitrile, nitro, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether), and urea (—NHCONHR—). The aforementioned groups can be elements of an R group as described herein, including R, $R^1$, $R^2$, $R^3$, $R^4$, and/or $R^5$. Additionally, one or more of the aforementioned groups can be explicitly excluded from a definition of one of the aforementioned R groups.

The term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

The Grubbs-Hoveyda catalyst refers to the Grubbs-Hoveyda catalyst, first generation (benzylidene-bis(tricyclohexylphosphine)dichlororuthenium, bis(tricyclohexylphosphine) benzylidine ruthenium(IV) dichloride) or second generation ((1,3-bis-(2,4,6-trimethylphenyl)-2-imidazolidinylidene) dichloro(o-isopropoxyphenylmethylene)ruthenium), each of which is available commercially from vendors such as Sigma-Aldrich (Milwaukee, Wis.). See U.S. Pat. No. 6,111,121 (Grubbs et al.) and U.S. Pat. No. 6,921,735 (Hoveyda et al.) for useful information and techniques for carrying out olefin cross metathesis reactions.

The term "stereoisomeric mixture" encompasses racemic mixtures as well as stereomerically enriched mixtures (e.g., R/S=30/70, 35/65, 40/60, 45/55, 55/45, 60/40, 65/35 and 70/30). The compounds described herein can be stereoisomeric mixture or they can be essentially stereomerically pure (>99% e.e.).

The term "stereomerically pure" refers to a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The term "protecting group" refers to any group which, when bound to a hydroxyl, nitrogen, or other heteroatom prevents undesired reactions from occurring at this group and which can be removed by conventional chemical or enzymatic steps to reestablish the hydroxyl group. The particular removable blocking group employed is not critical and preferred removable hydroxyl blocking groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyldiphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Included therein are nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, N.Y., 1994), which is incorporated herein by reference in its entirety. Some specific protecting groups that can be employed in conjunction with the methods of the invention are discussed below.

Unless otherwise indicated, an adjective before a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

COMPOUNDS AND METHODS OF THE INVENTION

The disclosure provides GEX1A derivative compounds and method of making such compounds, for example, based on the olefin-cross metathesis reaction. These compounds can have significant biological activity in regulating neurovisceral cholesterol homeostasis.

For compounds of Formula (I), the biological activity often rests in the alkyl chain that shares structural similarity to Formula (IV). Any ester group ($-C(=O)OR^1$) may be prone to metabolic cleavage without rendering the compounds biologically inactive. Thus, $R^1$ may be H, $CH_3$, a lower alkyl group, a cycloalkyl group, or an aryl group. Typically, $R^1$ is an alkyl group including, but not limited to, methyl, ethyl, propyl, butyl, pentyl, hexyl, heptyl, octyl, nonyl and decyl.

In one embodiment, compounds of Formula (II) and Formula (III) react under cross olefin metathesis reaction conditions in the presence of Grubbs-Hoveyda catalyst to provide a compound of Formula (I). The compounds of Formula (II) and Formula (III) can be prepared synthetically (e.g., from commercially available starting materials), or they can be prepared from cleavage and modification of a *Streptomyces chromofuscus* extract, such as GEX1A and derivatives thereof.

The invention also provides a pharmaceutical composition that includes a compound of any one of Formulas (I)-(IV), or a pharmaceutically acceptable salt thereof, and a pharmaceutically acceptable carrier. The pharmaceutical composition can also include other therapeutic agents that are compatible with the compound of the invention.

The compounds of the invention can be used in medical therapy, for example, where the medical therapy is the treatment of diseases that have an NPC-like cellular phenotype.

The disclosure further provides a method of treating a disease comprising contacting a cell with a compound of Formula (IV), wherein the compound is effective to regulate cholesterol homeostasis in a specific cell environment. The disclosure also provides a method to treat a subject in need thereof, comprising administering to the subject an effective amount of a compound of Formula (IV). The compound can be administered to the subject in a pharmaceutically acceptable excipient. The subject can be a human.

It should be noted that if there is a discrepancy between a depicted structure and a name given that structure, the structure should be accorded more weight. In addition, if the stereochemistry of a structure or a portion of a structure is not indicated with, for example, bold or dashed lines, the invention also includes all stereoisomers of the structure and the invention encompasses each stereoisomer and diastereomer of the illustrated structure. Moreover, any atom shown in a drawing with unsatisfied valences is assumed to be attached to enough hydrogen atoms to satisfy the valences.

General Synthetic Methods

The invention also relates to methods of making the compounds and compositions of the invention. The compounds and compositions can be prepared by any of the applicable techniques of organic synthesis. Many of these standard techniques are well known in the art. A variety of these techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as *March's Advanced Organic Chemistry: Reactions, Mechanisms, and Structure*, $5^{th}$ Ed., by M. B. Smith and J. March (John Wiley & Sons, New York, 2001); *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for preparation of the compositions of the invention are provided below. These methods are intended to illustrate the nature of such preparations are not intended to limit the scope of applicable methods. Other variations, such as adding various substituents (e.g., as defined above) on various alkyl, aryl, or heterocycle groups are included in the scope of the invention. Relevant starting materials can typically be purchased commercially (e.g., from Sigma-Aldrich, Milwaukee, Wis.) or prepared in a few standard steps from commercially available materials.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be $-100°$ C. to $200°$ C., as necessary for the reaction of interest, solvents will be aprotic or protic depending on the conditions required, and reaction times can be about 1 minute to about 10 days. Work-up typically consists of quenching any unreacted reagents followed by partition between a water/organic layer system (extraction) and separation of the layer containing the product of interest.

Oxidation and reduction reactions are typically carried out at temperatures near room temperature (about $23°$ C.), although for metal hydride reductions frequently the temperature is reduced to $0°$ C. to $-100°$ C. Heating can also be used when appropriate. Solvents are typically aprotic for reductions and may be either protic or aprotic for oxidations. Reaction times are adjusted to achieve desired conversions.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. A mammal includes a primate, human, rodent, canine, feline, bovine, ovine, equine, swine, caprine, bovine and the like. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Cultivation of GEX1A from *Streptomyces chromofuscus*

*Streptomyces chromofuscus*, ATCC 49982, was acquired from the ATCC and maintained on Bennett's Agar (0.1% yeast extract, 0.1% beef extract, 0.2% NZ amine A, 1% glucose, and 2% agar, pH 7.2), ISP2 Agar (1.0% malt extract, 0.4% yeast extract, 0.4% glucose, 2.0% agar), or Seed Medium (0.3% yeast extract, 0.5% tryptone). Production of GEX1A from *S. chromofuscus* was conducted in a developed GEX1A production medium (2.0% soy flour, 2.0% glucose, 0.05% yeast extract, 0.1% MgSO$_4$.7H$_2$O, 0.2% KH$_2$PO$_4$, 0.2% KNO$_3$, 0.05% NaCl, 0.015% CaCO$_3$, 0.0001% ZnSO$_4$.7H$_2$O, 0.018% Fe-EDTA, 2.0% Agar).

*S. chromofuscus* was inoculated onto ISP2 plates and incubated at 25° C. for 5 to 6 days. The fresh spores were then inoculated into 5 mL of Seed Medium and cultured at 30° C. with shaking for 4 days. The 5 mL seed culture was then spread onto GEX1A production medium plates and cultured at 25° C. for 7 to 10 days. After incubation, the plates were homogenized into 1 L dH$_2$O.

The crude aqueous extract was filtered via vacuum filtration through Whatman filter paper. Amberlite XAD-16 resin (2% w/v) was added to the filtered aqueous extract and left to stir for 24 hours. The extract was again filtered via vacuum filtration to obtain the Amberlite XAD-16 resin. The resin was suspended in methanol and left to stir for a period of 24 hours. The organic extract was then filtered via vacuum filtration and concentrated under reduced pressure. The crude organic material was purified via flash column chromatography (2-10% MeOH:DCM) to yield the desired compound as a pale yellow oil. NMR confirmed the compound to be GEX1A. GEX1A isolated yields were determined to be ~80-95 mg/L, significantly advancing the yields of 40-70 mg/L disclosed in previous literature methods.

Example 2

Synthesis of a Pyran Fragment (Formula III)

The synthesis of Formula IV can be accomplished as set forth in Scheme 1 below. A starting homoallylic alcohol 25 can be protected as its corresponding 2-naphthylmethoxymethyl ether. Exposure to classic ether transfer conditions would provide a terminal iodide, which can be used in an intramolecular radical cyclization reaction to produce a C1-C10 pyran fragment under classic tributyltin hydride/AIBN conditions. The naphthylmethyl ether can then be deprotected by mild aqueous oxidation conditions with DDQ. Barton deoxygenation and Stille cross coupling would complete the synthesis of the C1-C10 pyran fragment, which is a substructure of GEX1A analogues.

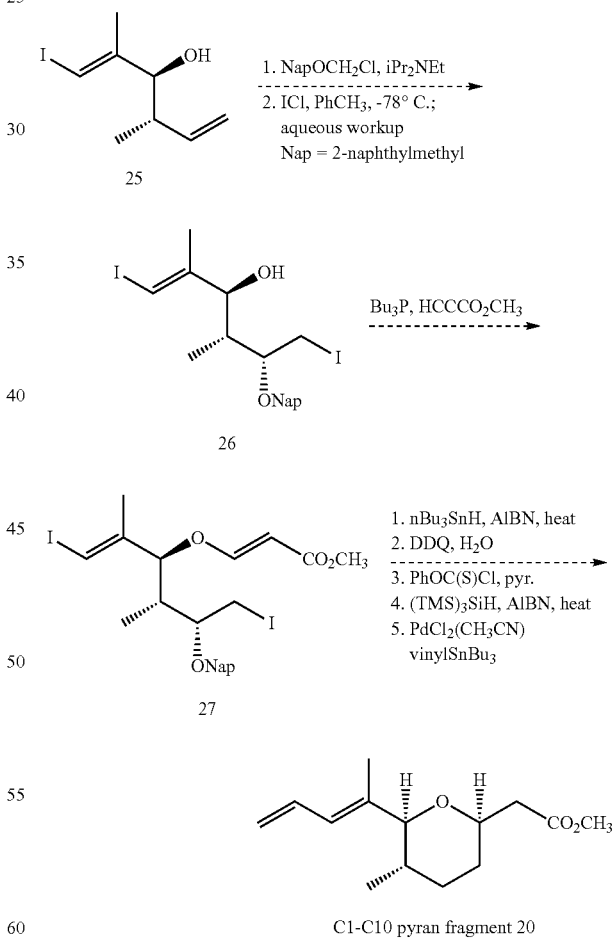

carbonate. Construction of the pyran can be completed by treating the solution with nBu₃SnH and AIBN, then with DDQ in H₂O, subsequently with PhOC(S)Cl, (TMS)₃SiH, AIBN, PdCl₂(CH₃CH), and vinylSnBu₃, to provide the compound of Formula III (20).

Example 3

Synthesis of an Epoxide Fragment (Formula II) and Coupling Reactions

Isobutyl lactate was protected at the secondary alcohol as benzyoxymethyl ether, as shown in Scheme 2. Exposure to a series of reduction-oxidation provides an aldehyde substrate (42) for a Keck diastereoselective crotylation. The compound then underwent methyl ether formation to provide olefin compound 40. Specifically, isobutyl lactate was treated with BOMCl, TBAI, and iPr₂NEt in CH₂Cl₂; then LAH in Et₂O; followed by Swern oxidation. The resulting aldehyde 42 was treated as shown in Scheme 2 in the presence of MgBr₂.Et₂O, KH, and CH₃I to yield alkene 40.

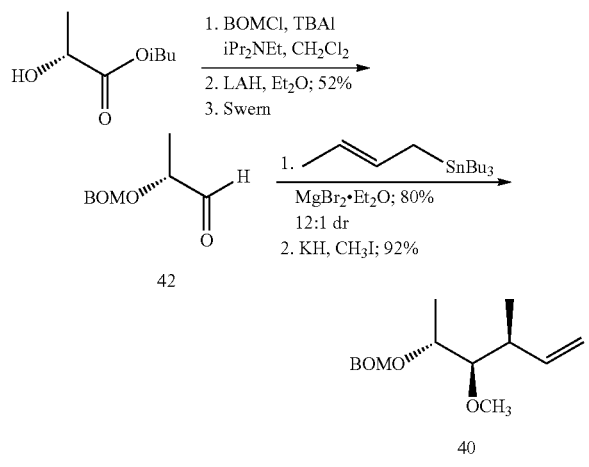

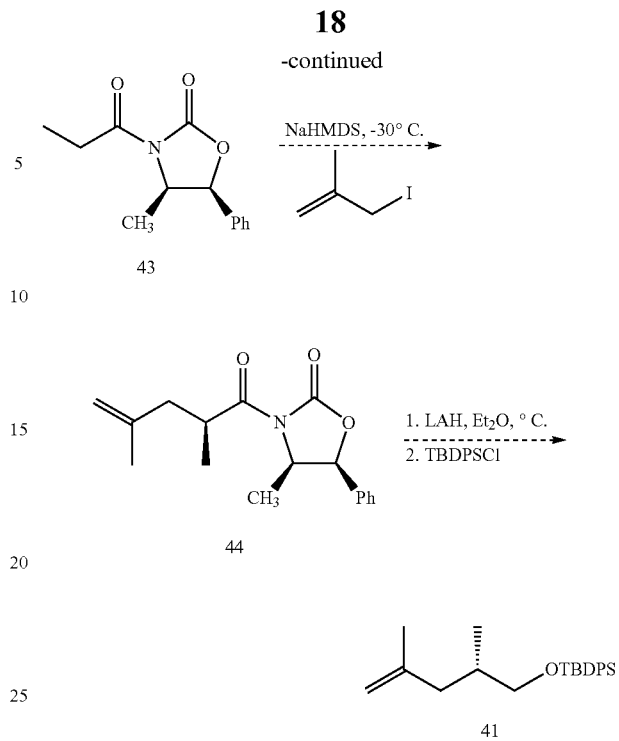

The 1,1-disubstituted alkene compound (41) can be separately prepared by generating sodium enolate from ephedrine-based propionate with methylallyl iodide in the presence of a strong base such as sodium hexamethyldisilazide. Reductive cleavage of the auxiliary of compound 44 can be followed by protection of the resulting primary alcohol as a tert-butyldiphenylsilyl ether to provide compound 41. Thus, an ephedrine-based propionate can be treated with NaHMDS and methylallyl iodide at −30° C. to provide compound 44. Compound 44 can then be treated with LAH in Et₂O, followed by TBDPSCl, to provide a 1,1-disubstituted alkene (41).

Compounds 40 and 41 can then joined by cross metathesis, for example, by exposure to Grubbs' second-generation metathesis catalyst, to provide the C14,C15-trisubstituted olefin 39, as illustrated in Schemes 3 and 4. A stereoselective epoxidation of olefin 39 directed by a free hydroxyl group at C18 can be carried out to complete the synthesis of the C11-C19 epoxide fragment 19 (a compound of Formula II).

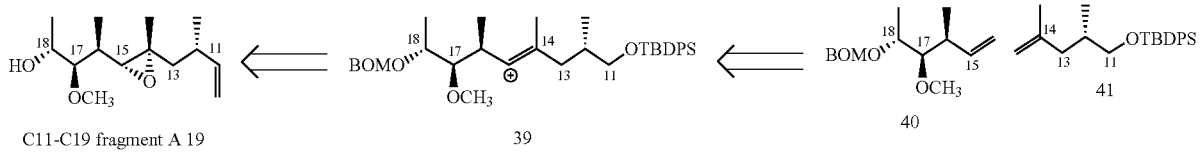

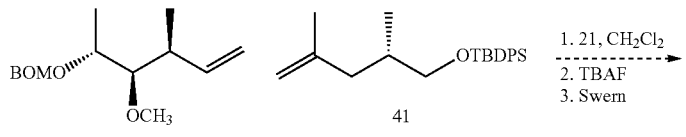

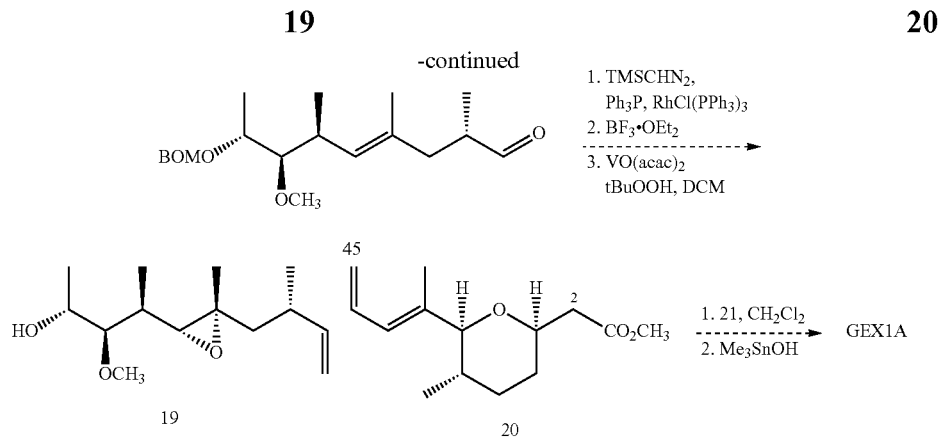

Various GEX1A derivatives (compounds of Formula I) can be synthesized from pyran fragment (compounds of Formula II) and epoxide fragments (compounds of Formula III) via olefin-cross metathesis. A variety of compounds of Formula I can be prepared by varying the R groups of the compounds of Formulas II and III to achieve the preparation of various novel compounds.

Example 4

Derivation of *Streptomyces chromofuscus* Extracts

The invention provides methods of preparing a compound of Formula (IV) from *Streptomyces chromofuscus* extracts. Extracts from *Streptomyces chromofuscus* such as GEX1A (herboxidiene) and various derivatives thereof can be cleaved in the presence of ethylene and a ruthenium metathesis catalyst, for example, as shown in Scheme 5.

Scheme 5. *Streptomyces chromofuscus* Extract Cleavage.

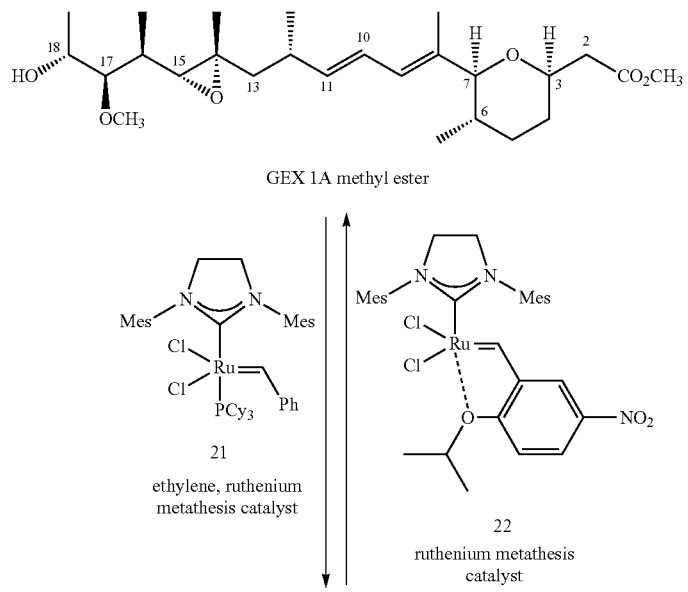

Cleavage of the extract can provide a compound of Formula II and a compound of Formula III. These compounds can be synthetically modified and then linked together using olefin cross metathesis to provide new compounds of Formula IV. Scheme 6 shows a specific divergent fragmentation and convergent total synthesis of GEX1A based on cross metathesis.

Scheme 6. Divergent Fragmentation and Convergent Total Synthesis of GEX1A.

-continued

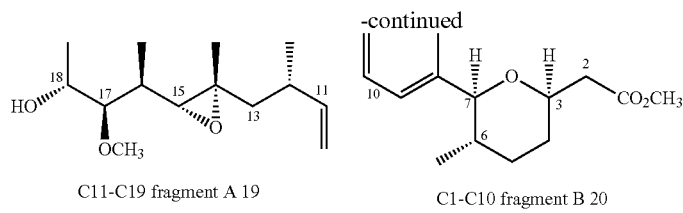

C11-C19 fragment A 19        C1-C10 fragment B 20

GEX1A can then be obtained by simple mild hydrolysis of the methyl ester.

Example 5

GEX1A Reversing Induced NPC1 Phenotype in HUVECS

Figure 2:
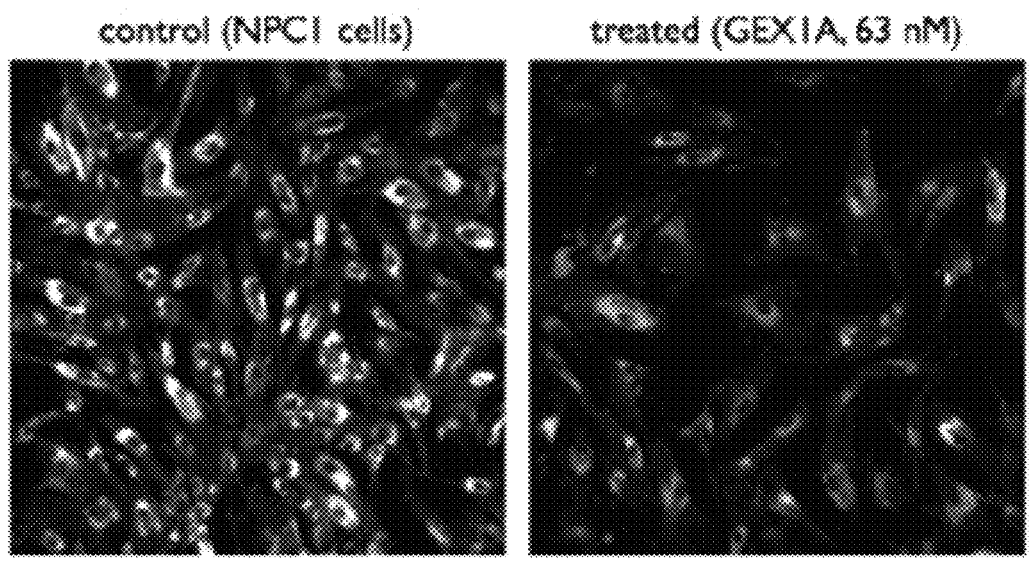
FIG. 2. Correction of the NPC1 phenotype with treatment of GEX1A.

GEX1A was evaluated for its ability to lower intracellular cholesterol levels in NPC1-mutant human fibroblasts (GM03123) through a previously described fluorescent imaging method (Pipalia et al., Automated microscopy screening for compounds that partially revert cholesterol accumulation in Niemann-Pick C cells. *J. Lipid Res.* (2006) 47: 284-301.). The treatment of GM03123 cells with GEX1A resulted in correction of the NPC1 phenotype as observed by reduced filipin staining in the cell. The fluorescent imaging results are presented in FIG. 2.

Compounds described herein were evaluated for their ability to lower intracellular cholesterol levels in NPC1-mutant human fibroblasts (GM03123) by the fluorescent imaging methods of Pipalia and coworkers.

Itraconazole, an anti-fungal agent, interferes with cholesterol trafficking and induces an NPC-like phenotype in human endothelial cells. Itraconazole (200 nM) was administered in two experiments with 100 nM GEX1A and 10 nM GEX1A, respectively. Filipin is used as a histochemical stain to visualize cholesterol in the cell line. Results show significant decrease in the amount of cholesterol in cell line in both dosages. An $IC_{50}$ value of 6 nm was obtained for GEX1A and similar values were obtained for GEX1A methyl ester.

Example 6

GEX1A Derivative Compounds Reversing Induced NPC1 Phenotype in HUVECS

To examine the effect of the GEX1A derivative compounds described herein, individual embodiment of the compounds can be administered to NPC1-mutant human fibroblasts (GM03123) in the above mentioned methods. Dosages ranging from 10 nM to 100 nM can be administered and observed at time points of 24-72 hours. It is postulated that these experiments will result in a significant correction of the NPC1 phenotype.

Example 7

Pladienolide Derivative Compounds Reversing Induced NPC1 Phenotype in HUVECS Pladienolide will be evaluated for its ability to lower intracellular cholesterol levels in NPC1-mutant human fibroblasts (GM03123) in the above mentioned methods. Dosages ranging from 10 nM to 100 nM can be administered and observed at time points of 24-72 hours. It is postulated that these experiments will result in a significant correction of the NPC1 phenotype.

Example 8

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |

| (xi) Topical Cream 2 | wt. % |
|---|---|
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of preparing a compound of Formula I:

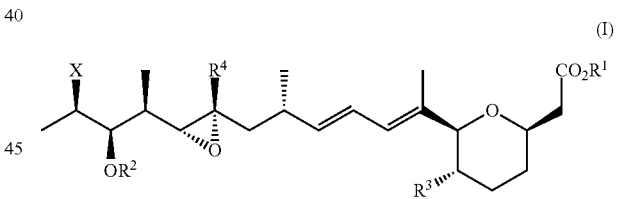

wherein
X is H, OH, or alkoxy;
$R^1$ is H, alkyl, cycloalkyl, amino, aryl, or heterocycle;
$R^2$ is H or $CH_3$;
$R^3$ is H or $CH_3$;
$R^4$ is H or $CH_3$; provided that one of $R^3$ and $R^4$ is H;
or a pharmaceutically acceptable salt thereof;
comprising contacting a compound of Formula II:

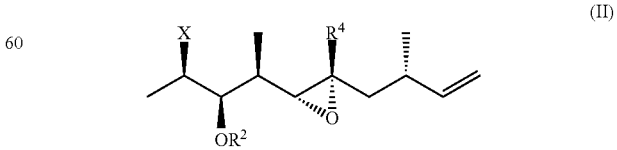

wherein X is H, OH, or alkoxy; and $R^2$ and $R^4$ are each independently H or $CH_3$;

and a compound of Formula III:

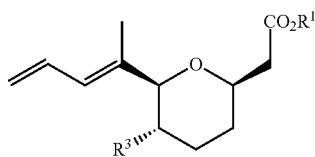

wherein R¹ is H, alkyl, cycloalkyl, amino, aryl, or heterocycle; and R³ is H or CH₃;
under olefin cross metathesis coupling conditions, to provide the compound of Formula I.

2. The method of claim 1 wherein the olefin cross metathesis coupling conditions comprise the presence of a Grubbs-Hoveyda catalyst.

3. The method of claim 2 wherein the Grubbs-Hoveyda catalyst is the second generation Grubbs-Hoveyda catalyst.

4. The method of claim 1 wherein X of Formula I is H.

5. The method of claim 1 wherein X of Formula I is OH.

6. The method of claim 1 wherein X of Formula I is OCH₃.

7. The method of claim 1 wherein R¹ of Formula I is H.

8. The method of claim 1 wherein R¹ of Formula I is alkyl.

9. The method of claim 1 wherein R¹ of Formula I is cycloalkyl, amino, aryl, or heterocycle.

10. The method of claim 1 wherein R² of Formula I is H.

11. The method of claim 1 wherein R² of Formula I is CH₃.

12. The method of claim 1 wherein R³ of Formula I is H.

13. The method of claim 1 wherein R³ of Formula I is CH₃.

14. The method of claim 1 wherein R⁴ of Formula I is H.

15. The method of claim 1 wherein R⁴ of Formula I is CH₃.

16. The method of claim 1 wherein the compound of Formula I is GEX1A:

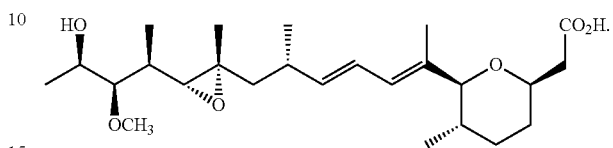

17. The method of claim 1 wherein the compound of Formula I is the GEX1A methyl ester:

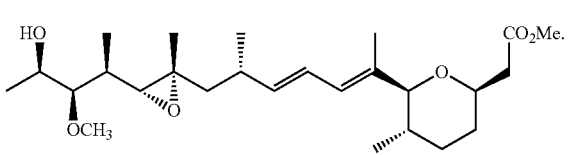

* * * * *